United States Patent

Stanier

[11] Patent Number: 5,891,473
[45] Date of Patent: Apr. 6, 1999

[54] GRANULAR COMPOSITIONS

[75] Inventor: Peter William Stanier, Sandbach, United Kingdom

[73] Assignee: Crosfield Limited, Warrington, England

[21] Appl. No.: 809,831

[22] PCT Filed: Sep. 9, 1995

[86] PCT No.: PCT/EP95/03560

§ 371 Date: Jul. 9, 1997

§ 102(e) Date: Jul. 9, 1997

[87] PCT Pub. No.: WO96/09033

PCT Pub. Date: Mar. 28, 1996

[51] Int. Cl.$^6$ ....................................................... A61K 9/14
[52] U.S. Cl. ........................... 424/489; 424/461; 424/435
[58] Field of Search ...................................... 424/440, 489, 424/466, 441, 461

[56] References Cited

U.S. PATENT DOCUMENTS

| | | |
|---|---|---|
| 4,089,943 | 5/1978 | Roberts et al. . |
| 5,286,480 | 2/1994 | Boggs et al. ............................. 424/440 |
| 5,380,530 | 1/1995 | Hill ......................................... 424/440 |

FOREIGN PATENT DOCUMENTS

| | | |
|---|---|---|
| 0269966B1 | 11/1987 | European Pat. Off. . |
| 268 763 | 6/1988 | European Pat. Off. . |
| 269 966 | 6/1988 | European Pat. Off. . |
| 272 380 | 6/1988 | European Pat. Off. . |
| 411 211 | 2/1991 | European Pat. Off. . |
| 473 171 | 3/1992 | European Pat. Off. . |
| 2 272 640 | 5/1994 | United Kingdom . |
| 92 02454 | 2/1992 | WIPO . |

*Primary Examiner*—Thurman K. Page
*Assistant Examiner*—William E. Benston, Jr.
*Attorney, Agent, or Firm*—Pillsbury Madison & Sutro, LLP

[57] ABSTRACT

Granular composition comprising 45 to 98% w/w of a water insoluble particulate, whereby 10 to 75% of the water insoluble particulate is made from a water insoluble particulate material, having a weight mean particle size of less than 20 microns and oil absorption capacity of 60 to 180 g/100 g and 10 to 75% of the water insoluble particulate is made from a water insoluble particulate material, having a weight mean particle size of below 20 microns and an oil absorption 200 to 350 g/100 g, the granular composition having a particle size, by sieve analysis, of 95% below 600 microns and 90% above 40 microns.

10 Claims, No Drawings

GRANULAR COMPOSITIONS

This application is the national phase of international application PCT/EP95/03560 filed Sep. 9, 1995 WO90/09033, Mar. 28, 1996 which designated the U.S.

FIELD OF THE INVENTION

The present invention relates to granular compositions which provide useful sensorially-perceived benefits in toothpaste compositions.

BACKGROUND OF THE INVENTION

The use of water as a binder for silica particles has been disclosed in GB1,365,516 and water is known as a common binder for size enlargement (Handbook of Powder Technology—Vol 1—Particle Size Enlargement—page 41, Table 2.3—Elsevier).

Toothpaste formulations containing a granular composition comprising a water insoluble material and a water insoluble binder have been disclosed in EP-B-269,966. Such granular composition can contain functional substances such as medicaments, enzymes and polishing agents. The problem addressed by this document is that it is not possible to bind the particles within the granular composition with water soluble binders for use in formulations containing large amounts of water, such as toothpastes. The reason being that the water soluble binder will dissolve in the aqueous component of the formulation and weaken the granular composition making it impossible to detect the coarse particles in the mouth.

The addition of a zinc salt, as an anti-plaque agent, into a toothpaste composition has already been disclosed in GB 1,373,001.

It has been found that granule compositions containing only water insoluble particulates of low to medium structure, particularly those with low oil absorption capacity favored as abrasives and polishing agents in dental formulations, bound together with water and dried are too weak to survive the normal processes in toothpaste manufacture and therefore would not be felt in the subsequent tooth cleaning process.

Additionally, granule compositions containing high structured water insoluble particulates (i.e. with high oil absorption capacity) for example silicas favored as thickening agents in toothpaste formulations, are considered to have too much strength and give unacceptable levels of mouthfeel.

To overcome this problem it has been discovered that granular compositions of sufficient strength can be prepared by mixing a high structured water insoluble particulate with a low to medium structured one prior to the binding process. Surprisingly the addition of powdered therapeutic agents e.g. zinc citrate, opacifiers e.g. titanium dioxide and coloured pigments have been shown to have no significant detrimental effect on the properties of the granular composition.

STANDARD PROCEDURES

The granular compositions of the invention are defined in terms of the properties and texture of the water insoluble particulates used to produce the agglomerate, its particle size distribution, and strength.

i) Oil Absorption

The oil absorption is determined by the ASTM spatula rub-out method (American Society Of Test Material Standards D, 281).

The test is based on the principle of mixing linseed oil with the water insoluble particulate by rubbing with a spatula on a smooth surface until a stiff putty-like paste is formed which will not break or separate when it is cut with a spatula. The volume of oil used is converted to weight and expressed as g of oil/100 g of water insoluble particulate.

ii) Weight Mean Particle Size

The weight mean particle size of the water insoluble particulate before agglomeration is determined using a Malvern Mastersizer model X, made by Malvern Instruments, Malvern, Worcestershire with MS15 sample presentation unit. This instrument uses the principle of mie scattering, utilising a low power He/Ne laser. The water insoluble particulates are dispersed ultrasonically in water for 5 minutes to form an aqueous suspension and then mechanically stirred before they are subjected to the measurement procedure outlined in the instruction manual for the instrument, utilising a 45 mm lens in the detector system.

The Malvern Particle Sizer measures the weight particle size of the water insoluble particulate. The weight mean particle size ($d_{50}$) or 50 percentile, the 10 percentile ($d_{10}$) and the 90 percentile ($d_{90}$) are easily obtained from the data generated by the instrument.

iii) Granule Composition Strength

The weight mean particle size distribution of the granular composition is measured using the same Malvern instrument and general method described above, but with the following differences:

a) the granules are measured with a 300 mm lens in the detector system.

b) an initial particle size distribution of the granules is taken with no ultrasonic dispersion (0 ultrasonics) i.e. sample dispersed with mechanical stirring only.

c) the granules are dispersed using ultrasonics for two minutes, setting 50, and then subjected to the usual measurement procedure (50 ultrasonics).

d) the granules are dispersed using ultrasonics for two minutes, setting 100, and then subjected to the usual measurement procedure (100 ultrasonics).

The d10, d50 and d90 can then be interpolated from the particle size distribution generated by the instrument and the higher the values obtained after the exposure to ultrasonics the stronger the granular composition.

iv) Particle Size Distribution by Sieve Analysis

A more accurate measure of the true particle size distribution of the granular composition is done using sieve analysis.

100 g of the sample is placed on the top sieve of a series of BS sieves, at approximately 50 micron intervals between 45 and 600 microns. The sieves are arranged in order with the finest at the bottom and the coarsest at the top of the stack. The sieves are placed in a mechanical vibrator e.g. Inclyno Mechanical Sieve Shaker by Pascall Engineering Co Ltd., covered with a lid and shaken for 10 minutes.

Each sieve fraction is accurately weighed and the results calculated:

$$\% \text{ residue} = \frac{\text{Wt. of residue} * 100}{\text{Wt. of sample}}$$

A particle size distribution can then be plotted from the data.

GENERAL DESCRIPTION OF THE INVENTION

It is a first object of the present invention to provide a granular composition comprising 45 to 98% w/w of a water insoluble particulate, whereby 10 to 75% of the water insoluble particulate is made from a water insoluble particulate material, having a weight mean particle size of less than 20 microns and an oil absorption capacity of 60 to 180 g/100 g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice and 10 to 75% of the water insoluble particulate is made from a water insoluble particulate material, having a weight mean particle size of below 20 microns and an oil absorption 200 to 350 g/100 g, selected from the group consisting of amorphous silicas, low density aluminas and expanded perlites, the granular composition having a particle size, by sieve analysis, of 95% below 600 microns and 95% above 40 microns.

This granular composition is substantially free of organic or inorganic binder.

It is preferable that the granular composition should have a particle size distribution, as measured by sieve analysis, such that 95% of the granules are less than 400 microns and 95% of the particles are above 100 microns, most preferably 150 microns.

Owing to the porous nature of the agglomerates, it is possible for them to act as delivery vehicles for substances that give cosmetic benefits such as coloring pigments, flavors, perfumes or other cosmetic. The agglomerates can also ontain other cosmetic and/or therapeutic dental and/or oral actives and release them into mouth. Such substances may be contained within the pores of the material. The inclusion of a material having a therapeutic or cosmetic effect on the gums or teeth or oral cavity into these agglomerates provides for a further benefit in that upon crushing or collapsing of these agglomerates, the therapeutic/cosmetic agent is slowly released, thus delivering the therapeutic agent over to the mouth over a longer period of time. Suitable examples of such therapeutic agents are zinc salts such as zinc citrate; antimicrobial agents such as Triclosan; anti-caries agents such as sodium fluoride and sodium monofluorophosphate; anti-plaque agents such as stannous pyrophosphate etc.

In this respect it has surprisingly been found, that the inclusion of zinc citrate in the agglomerates (in an amount of up to 15%, preferably up to 12% by weight of the agglomerates) significantly reduced the level of astringency, perceived by trained panellists upon testing a toothpaste with such agglomerates for their sensory properties.

The addition of $TiO_2$ as an opacifying agent at a concentration of 1 to 5% w/w, usually at the expense of the water insoluble particulates, ensures that the granules have a white appearance and therefore stand out in coloured toothpaste formulations.

If coloured granules are required, then suitable food grade coloured pigments, for example pigment dispersions under the Cosmenyl trade name or pigment powders under the Hostaperm trade name or Cosmetic Pink RC 01 (D & C Red No 30) supplied by Hoechst, can be added to the composition of the granule, without affecting the strength of the granule.

If titanium dioxide and therapeutic agent are omitted from the granular composition containing abrasive and thickening silicas, then the coarse particles are invisible in transparent gel formulations.

Moreover, the agglomerate strength can be varied over a wide range by changing the water insoluble particulate structure, i.e. low structure water insoluble particulates decrease strength whereas high structure water insoluble particulates increase agglomerate strength.

The use of water insoluble particulates which already have an approved role in toothpastes formulations, such as toothpaste abrasive silicas [e.g. Sorbosil AC77 (obtainable from Crosfield Limited—England)] as the low/medium structure component, is an added advantage since such silicas are capable of providing extra cleaning to the formulation and have good compatibility with the formulation. Indeed, particularly preferred water insoluble particulates which make up the granular composition are mixtures of synthetic, amorphous thickening [e.g. Sorbosil TC15 (obtainable from Crosfield Limited—England)] and abrasive silicas.

The agglomerates should be insoluble in the medium of the toothpaste composition into which it is incorporated. In this context, "insoluble" means having insufficient solubility at ambient temperature in that the agglomerates remain undissolved or substantially undissolved in the composition such that their friability under the conditions of use of the composition and thus their ability to perform their cleaning/polishing function are not deleteriously affected. Preferably, the level of insolubility of the agglomerates extend to their insolubility in the oral environment in which the composition is used, which may frequently contain higher levels of water than for example a toothpaste, owing to the presence of saliva and added water frequently used in the brushing regime.

When the granules are incorporated in a toothpaste composition, it is important that they break down under the shear forces generated by the toothbrush in a relatively short period of time, whereby the gritty feel experienced by the user is eliminated.

This means, that the agglomerates should have a particle strength such that they will collapse within the range of shear and/or crush forces normally produced in the relevant brushing regime, since the considerably variable forces produced at a particular location over time enable at least some of the agglomerates to survive intact long enough to perform their cleaning function to a satisfactory degree.

It is even possible to tailor the breakdown time of the agglomerates, such as to control the contact time for a given duration of brushing of the composition, by controlling the average crush strength of the agglomerates, for example by selecting a particular type of source of the particulate materials and/or the manner in which they agglomerate in the manufacturing process.

When the agglomerates break up under the action of shear and/or crush forces, the resulting average particle size (diameter) will typically be less than about 40 microns. Such reduced particle sizes will generally avoid any feeling of grittiness in the mouth, and impart a feeling of polished teeth.

It is another object of the present invention to provide a process for producing a granular composition wherein, 10 to 75 parts by weight of a water insoluble particulate material, having a weight mean particle size of less than 20 microns and an oil absorption capacity of 60 to 180 g/100 g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice are mixed with 10 to 75 parts by weight of a water insoluble particulate material, having a weight mean particle size of below 20 microns and an oil absorption 200 to 350 g/100 g, selected from the group consisting of amorphous silicas, low density aluminas and expanded perlites, then agglomerated with water, the resulting product being then dried.

Preferably, the water insoluble particulate powders are high and low to medium structure amorphous silica particles and a therapeutic agent is mixed with them prior to agglomeration. If opaque granules are required, then $TiO_2$ is added to the powder mixture. If coloured granules are required, a suitable food grade coloured pigment dispersion can be added.

By drying the product after agglomeration, a granular composition is obtained which is stable in a toothpaste composition.

Agglomeration can be achieved for example by pan granulation, extrusion, spray granulation or spinning disc granulation.

Preferably, the agglomeration is operated in a pan granulator, when the water:solids (i.e. water insoluble particulates with optionally $TiO_2$/therapeutic agent etc. blended) ratio is in the range 1.1–1.35:1. This ratio is important to achieve agglomerates of correct strength, since below this the material remains a powder and above this a paste is formed.

Then the agglomerates are dried. This drying can be done in several ways, e.g. in an oven or in a fluidized bed. During this drying stage, the required degree of strength is built into the agglomerates.

It has also been found that agglomeration can be achieved by compacting the powder mixture and in this process a drying stage is not required.

It is therefore another object of the present invention to provide a process for producing a granular composition wherein, 10 to 75 parts by weight of a water insoluble particulate material, having a weight mean particle size of less than 20 microns and an oil absorption capacity of 60 to 180 g/100 g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice are mixed with 10 to 75 parts by weight of a water insoluble particulate material, having a weight mean particle size of below 20 microns and an oil absorption 200 to 350 g/100 g, selected from the group consisting of amorphous silicas, low density aluminas and expanded perlites, the resulting blend being agglomerated by compaction.

For incorporation into toothpastes, it is important that virtually all particles are below 600 $\mu$m, preferably below 400 $\mu$m since gritty particles give unpleasant mouthfeel properties. A size reduction step utilizing minimum energy to prevent unnecessary breakdown of the agglomerate is therefore required.

One or more sieving steps are then desirable to ensure no oversize material and also to provide a bottom cut at e.g. 150 microns.

SPECIFIC DESCRIPTION OF THE INVENTION

The present invention will be further illustrated in the following examples.

Comparative Example 1

Two silicas of high structure [Sorbosil TC15 (obtainable from Crosfield Limited—England)] and medium (bordering upon low) structure [Sorbosil AC77 (obtainable from Crosfield Limited—England)] were agglomerated individually at 200 g powder batch size, laboratory scale with de-ionised water (water:solids ratio of 1.33:1) using a Sirman CV6 mixer, supplied by Metcalfe Catering Equipment Ltd, Blaenau Ffestiniog, Wales.

The resulting wet agglomerates were then dried in an oven at 150° C. for 4 hours, gently forced through a 420 micron screen and sieved at 150 microns to adjust the particle size distribution.

The silicas have the following properties:

| PROPERTY | | SORBOSIL TC15 (*) | SORBOSIL AC77 (*) |
|---|---|---|---|
| OIL ABSORPTION (g/100 g) | | 315 | 120 |
| WEIGHT MEAN | $d_{10}$ | 5.6 | 2.7 |
| PARTICLE SIZE | $d_{50}$ | 12.9 | 8.1 |
| (microns) | $d_{90}$ | 29.3 | 17.8 |
| SURFACE AREA ($m^2g^{-1}$) | | 260 | 120 |

(*)-obtainable from Crosfield Limited - England

The granular silicas after agglomeration have the following properties:

| | Ultrasonics | d10 | d50 | d90 |
|---|---|---|---|---|
| Sorbosil TC15 | 0 | 268 | 415 | 549 |
| | 50 | 249 | 410 | 553 |
| | 100 | 70 | 265 | 469 |
| Sorbosil AC77 | 0 | 16 | 187 | 346 |
| | 50 | 3.2 | 10 | 37.4 |
| | 100 | 2.9 | 8.5 | 21.2 |

The high structured silica TC15 (obtainable from Crosfield Limited—England) forms an agglomerate which is too strong and will not break down in the required time with brushing in a toothpaste composition, whilst the medium/low structured silica AC77 (obtainable from Crosfield Limited—England) produces an agglomerate which is too weak to survive the normal processes in toothpaste manufacture.

Example 1

The silicas used in comparative example 1 were blended together with titanium dioxide in the following matrix, which includes the individual silicas with $TiO_2$:

| | Comp. 1 parts by wt | Comp. 2 parts by wt | Comp. 3 parts by wt | Comp. 4 parts by wt | Comp. 5 parts by wt |
|---|---|---|---|---|---|
| SORBOSIL TC15 (*) | 97.0 | 72.75 | 48.5 | 24.25 | 0 |
| SORBOSIL AC77 (*) | 0 | 24.25 | 48.5 | 72.75 | 97.0 |
| $TiO_2$ | 3.0 | 3.0 | 3.0 | 3.0 | 3.0 |

(*)-obtainable from Joseph Crosfield & Sons - England

De-ionised water was added to the powder mixes to give a water:solids ratio of 1.33 to 1 and the resulting 200 g blends were agglomerated using a laboratory scale Sirman CV6 mixer, supplied by Metcalfe Catering Equipment Ltd, Blaenau Ffestiniog, Wales.

The resulting wet agglomerates were then dried in an oven at 150° C. for 4 hours, gently forced through a 420 micron screen and sieved at 150 microns to adjust the particle size distribution.

The resultant agglomerates have the following properties:

|  | Ultrasonics | d10 | d50 | d90 |
|---|---|---|---|---|
| Composition 1 | 0 | 258 | 404 | 555 |
|  | 50 | 254 | 389 | 547 |
|  | 100 | 128 | 309 | 500 |
| Composition 2 | 0 | 228 | 370 | 542 |
|  | 50 | 201 | 355 | 530 |
|  | 100 | 118 | 277 | 474 |
| Composition 3 | 0 | 207 | 351 | 534 |
|  | 50 | 167 | 320 | 509 |
|  | 100 | 5.3 | 73 | 220 |
| Composition 4 | 0 | 176 | 324 | 506 |
|  | 50 | 4 | 15.6 | 71 |
|  | 100 | 3.4 | 11 | 29.8 |
| Composition 5 | 0 | 8.8 | 186 | 332 |
|  | 50 | 2.8 | 9.4 | 31.6 |
|  | 100 | 2.6 | 8.3 | 21.1 |

Compositions 1 & 5 show that the addition of $TiO_2$ has no detrimental effect on particle strength of the agglomerate. It can be seen that particle strength varies according to the relative amounts of high and medium/low structure silicas present in the agglomerate. Compositions 1 & 2 are considered to be too strong and compositions 4 & 5 too weak for an optimum strength granule. Composition 3, whilst not optimum is considered to be within the desired range for strength.

Example 2

The following powders were blended together to give an intimate mixture:

|  | 1 parts by weight | 2 parts by weight |
|---|---|---|
| Sorbosil AC77 (*) | 43.15 | 48.5 |
| Sorbosil TC15 (*) | 43.15 | 48.5 |
| Titanium Dioxide | 3.0 | 3.0 |
| Zinc citrate trihydrate | 10.7 | 0 |

(*)-obtainable from Crosfield Limited - England

Water was added to this mixture to give a water:solids ratio of 1.33 to 1, the resulting blend being granulated in a 100 liter CMG mixer/granulator made by Eurovent Ltd, Fenton, Stoke-on-Trent, with a 6 Kg batch charge.

The resulting wet agglomerates were then partially dried for 30 minutes in a fluid bed drier and finished in an oven for 2 hours at a temperature of 120° C. The particle size distribution was adjusted by screening at 150 and 400 microns. The properties of the granular composition are outlined below.

|  | Ultrasonics | d10 | d50 | d90 |
|---|---|---|---|---|
| Composition 1 | 0 | 193 | 334 | 502 |
|  | 50 | 112 | 289 | 475 |
|  | 100 | 3.3 | 14.3 | 41.5 |
| Composition 2 | 0 | 268 | 391 | 539 |
|  | 50 | 224 | 365 | 526 |
|  | 100 | 3.3 | 12 | 39 |

Clearly, the presence of zinc citrate has little effect on the strength of the granular compositions and granules of this strength have been shown to survive the normal processing conditions used in toothpaste manufacture, be stable in and have good sensory properties in a toothpaste composition.

Examples 3–7

The following homogeneous powder blends were made:

| INGREDIENT | EX 3 | EX 4 | EX 5 | EX 6 | EX 7 |
|---|---|---|---|---|---|
| SORBOSIL AC77 | 41.0 | 36.0 | 24.5 | 40.3 | 47.85 |
| SORBOSIL TC15 | 41.0 | 36.0 | 24.5 | 13.4 | 47.85 |
| TRICLOSAN | 4.3 |  |  |  | 4.3 |
| STANNOUS PYROPHOSPHATE |  | 14.3 |  |  |  |
| ZINC CITRATE TRIHYDRATE | 10.7 | 10.7 | 6.3 |  |  |
| TITANIUM DIOXIDE | 3.0 | 3.0 | 3.0 | 3.0 |  |
| POTASSIUM NITRATE |  |  | 41.7 |  |  |
| POTASSIUM CITRATE |  |  |  | 43.3 |  |

De-ionised water was added to the powder mixes (200 g) to give a water:solids ratio of 1.33 to 1 for examples 3, 4 & 7 and 0.72 to 1 for examples 5 & 6. The resulting blends were agglomerated using a laboratory scale Sirman CV6 mixer, supplied by Metcalfe Catering Equipment Ltd, Blaenau Ffestiniog, Wales. The resulting wet agglomerates were then dried in an oven at 150° C. for 12 hours, gently forced through a 420 micron screen and sieved at 150 microns to adjust the particle size distribution.

The resultant agglomerates have the following properties:

|  | Ultrasonics | d10 | d50 | d90 |
|---|---|---|---|---|
| Example 3 | 0 | 186 | 306 | 488 |
|  | 50 | 14 | 222 | 425 |
|  | 100 | 3.8 | 23 | 62 |
| Example 4 | 0 | 223 | 385 | 530 |
|  | 50 | 9.4 | 151 | 423 |
|  | 100 | 4 | 16 | 41 |
| Example 5 | 0 | 32 | 233 | 460 |
|  | 50 | 11 | 128 | 376 |
|  | 100 | 3.9 | 17 | 45 |
| Example 6 | 0 | 199 | 386 | 554 |
|  | 50 | 8 | 180 | 412 |
|  | 100 | 3 | 13 | 41 |
| Example 7 | 0 | 190 | 346 | 532 |
|  | 50 | 30 | 286 | 510 |
|  | 100 | 4 | 16 | 46 |

Examples 8–10

The following homogeneous powder blends were made:

| INGREDIENT | EX 8 | EX 9 | EX 10 |
|---|---|---|---|
| SORBOSIL AC77 | 26.3 | 43.1 | 60.0 |
| SORBOSIL TC15 | 26.3 | 43.1 | 40.0 |
| POTASSIUM PYROPHOSPHATE | 24.6 |  |  |
| SODIUM PYROPHOSPHATE | 19.8 |  |  |
| ZINC CITRATE TRIHYDRATE |  | 10.8 |  |
| TITANIUM DIOXIDE | 3.0 | 3.0 |  |

The powder blends were fed through a roller compactor Fitzpatrick. Chilsonator model L83 (made by Fitzpatrick Company, Elmhurst, Ill., USA) which was configured as FIG. 1 in the article "Preconditioning process powders with dry granulation" by Calvin E. Johnson (The Fitzpatrick Company), cited in Powder and Bulk Engineering December 1987. The upper screen size was 425 microns and the lower one was 250 microns.

The resultant agglomerated product had the following properties:

|            | Ultrasonics | d10 | d50 | d90 |
|------------|-------------|-----|-----|-----|
| Example 8  | 0           | 150 | 326 | 526 |
|            | 50          | 17  | 162 | 383 |
|            | 100         | 4   | 29  | 69  |
| Example 9  | 0           | 176 | 331 | 530 |
|            | 50          | 74  | 292 | 516 |
|            | 100         | 6.9 | 72  | 314 |
| Example 10 | 0           | 160 | 300 | 497 |
|            | 50          | 120 | 288 | 495 |
|            | 100         | 3   | 15  | 69  |

Examples 11–14

The following homogeneous powder blends were made:

| INGREDIENT          | EX 11 | EX 12 | EX 13 | EX 14 |
|---------------------|-------|-------|-------|-------|
| GASIL 23D           |       | 72.75 | 36.0  | 64.9  |
| GASIL 23TP          | 50.0  |       |       |       |
| SORBOSIL AC35       |       | 24.25 | 12.0  | 21.6  |
| GASIL 200TP         | 50.0  |       |       |       |
| TITANIUM DIOXIDE    |       | 3.0   | 2.6   | 2.6   |
| POTASSIUM CITRATE   |       |       | 43.3  |       |
| ZINC CITRATE TRIHYDRATE |   |       | 6.1   | 10.9  |

De-ionised water was added to the powder mixes (200 g) to give a water:solids ratio of 1.33 to 1 for examples 11,12 & 14 and 0.72 to 1 for example 13. The resulting blends were agglomerated using a laboratory scale Sirman CV6 mixer, supplied by Metcalfe Catering Equipment Ltd, Blaenau Ffestiniog, Wales.

The resulting wet agglomerates were then dried in an oven at 150° C. for 12 hours, gently forced through a 420 micron screen and sieved at 150 microns to adjust the particle size distribution.

The resultant agglomerates have the following properties:

|            | Ultrasonics | d10 | d50 | d90 |
|------------|-------------|-----|-----|-----|
| Example 11 | 0           | 197 | 354 | 526 |
|            | 50          | 10  | 213 | 465 |
|            | 100         | 3.3 | 15  | 50  |
| Example 12 | 0           | 187 | 311 | 498 |
|            | 50          | 16  | 250 | 471 |
|            | 100         | 5   | 34  | 297 |
| Example 13 | 0           | 190 | 333 | 518 |
|            | 50          | 14  | 210 | 455 |
|            | 100         | 4   | 24  | 69  |
| Example 14 | 0           | 196 | 326 | 514 |
|            | 50          | 96  | 282 | 476 |
|            | 100         | 4   | 29  | 104 |

Examples 15–16

The following homogeneous powder blends were made:

| INGREDIENT            | EX 15 | EX 16 |
|-----------------------|-------|-------|
| BACO AF239            | 50.0  |       |
| CALCIUM PYROPHOSPHATE |       | 50.0  |
| SORBOSIL TC15         | 50.0  | 50.0  |

De-ionised water was added to the powder mixes (200 g) to give a water:solids ratio of 1.33 to 1. The resulting blends were agglomerated using a laboratory scale Sirman CV6 mixer, supplied by Metcalfe Catering Equipment Ltd, Blaenau Ffestiniog, Wales.

The resulting wet agglomerates were then dried in an oven at 150° C. for 12 hours, gently forced through a 420 micron screen and sieved at 150 microns to adjust the particle size distribution.

The resultant agglomerates have the following properties:

|            | Ultrasonics | d10 | d50 | d90 |
|------------|-------------|-----|-----|-----|
| Example 15 | 0           | 219 | 379 | 536 |
|            | 50          | 194 | 355 | 524 |
|            | 100         | 6.7 | 43  | 186 |
| Example 16 | 0           | 215 | 373 | 534 |
|            | 50          | 177 | 339 | 517 |
|            | 100         | 3   | 37  | 95  |

Examples 17–19

The following blends were made:

| INGREDIENT              | EX 17 | EX 18 | EX 19  |
|-------------------------|-------|-------|--------|
| SORBOSIL AC77           | 44.2  | 43.9  | 44.45  |
| SORBOSIL TC15           | 44.1  | 43.9  | 44.45  |
| ZINC CITRATE TRIHYDRATE | 11.0  | 10.7  | 11.76  |
| COSMENYL BLUE A2R       | 0.7   |       | 0.07   |
| COSMENYL GREEN GG       |       |       | 0.27   |
| COSMETIC PINK RC 01     |       | 1.5   |        |

De-ionised water was added to the powder mixes (200 g) to give a water:solids ratio of 1.33 to 1. With examples 17 & 19, the Cosmenyl pigment dispersions were added to the de-ionised mixing water, which was then added to the powder mix. The resulting blends were agglomerated using a laboratory scale Sirman CV6 mixer, supplied by Metcalfe Catering Equipment Ltd, Blaenau Ffestiniog, Wales.

The resulting wet agglomerates were then dried in an oven at 150° C. for 12 hours, gently forced through a 420 micron screen and sieved at 150 microns to adjust the particle size distribution.

The resultant agglomerates have the following properties:

|            | Ultrasonics | d10 | d50 | d90 |
|------------|-------------|-----|-----|-----|
| Example 17 | 0           | 182 | 301 | 487 |
|            | 50          | 41  | 251 | 447 |
|            | 100         | 4   | 22  | 62  |
| Example 18 | 0           | 191 | 344 | 532 |
|            | 50          | 163 | 347 | 534 |
|            | 100         | 5.6 | 39  | 210 |

-continued

|  | Ultrasonics | d10 | d50 | d90 |
|---|---|---|---|---|
| Example 19 | 0 | 192 | 345 | 537 |
|  | 50 | 77 | 285 | 511 |
|  | 100 | 4 | 19 | 49 |

Example 20

A toothpaste having the following composition was produced.

| INGREDIENT | % BY WEIGHT |
|---|---|
| Sorbitol | 45 |
| Water | 22.12 |
| Sorbosil AC77 | 10.0 |
| Silica of the Invention | 7.0 |
| Sorbosil TC15 | 6.0 |
| PEG 1500 | 5.0 |
| SLS | 1.5 |
| $TiO_2$ | 1.0 |
| Spearmint Flavour DP5017 | 0.5 |
| SMPF | 0.8 |
| SCMC | 0.8 |
| Saccharin | 0.2 |
| Sodium Benzoate | 0.08 |

The above formulation was made under vacuum using conventional preparative procedures in a Lang mixer. In preparation 1 the flavor component was added over the side of the vessel near the end of the formulation.

A further identical preparation 2 was carried out except that the flavor was added to the silica granule of the invention by pipette prior to its introduction to the toothpaste mixer. The granule of the invention, containing the flavor, was dry mixed with the other two silicas and the resultant powder mix was added in portions over 40 minutes under closed vacuum.

The two pastes were then examined "blind" by 6 people, who were asked to assess the taste properties. All 6 people stated that paste 2 had a significantly stronger spearmint taste than paste 1, indicating that the granule of the invention could carry and deliver flavor more effectively than simply adding it to the toothpaste mix separately.

I claim:

1. Granular composition comprising 45 to 98% w/w of a water insoluble particulate, whereby 10 to 75% of the water insoluble particulate comprises a water insoluble particulate material having a weight mean particle size of less than 20 microns and an oil absorption capacity of 60 to 180 g/100 g, and is selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice, and 10 to 75% of the water insoluble particulate comprises a water insoluble particulate material having a weight mean particle size of below 20 microns and an oil absorption 200 to 350 g/100 g, selected from the group consisting of amorphous silicas, low density aluminas and expanded perlites, the granular composition having a particle size, by sieve analysis, of 95% below 600 microns and 95% above 40 microns.

2. Granular composition according to claim 1 comprising 1 to 5% w/w of $TiO_2$.

3. Granular composition according to claim 1 comprising up to 15% zinc citrate.

4. Granular composition according to claim 1 wherein the agglomerate contains a material having a cosmetic or therapeutic dental benefit.

5. Granular composition according to claim 1 wherein the material having a cosmetic or therapeutic benefit is a flavor compound.

6. Granular composition according to claim 1 comprising a high structure silica thickener and a low structure silica abrasive.

7. Process for producing a granular composition according to claim 1 wherein, 10 to 75 parts by weight of a water insoluble particulate material, having a weight mean particle size of less than 20 microns and an oil absorption capacity of 60 to 180 g/100 g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice are mixed with 10 to 75 parts by weight of a water insoluble particulate material, having a weight mean particle size of below 20 microns and an oil absorption 200 to 350 g/100 g, selected from the group consisting of amorphous silicas, low density aluminas and expanded perlites, then agglomerated with water, the resulting product being then dried.

8. Process for producing a granular composition wherein, 10 to 75 parts by weight of a water insoluble particulate material, having a weight mean particle size of less than 20 microns and an oil absorption capacity of 60 to 180 g/100 g, and selected from the group consisting of amorphous silicas, aluminas, calcium carbonates, dicalcium phosphate, tribasic calcium phosphates, insoluble sodium metaphosphate, calcium pyrophosphates, hydroxyapatites, perlites, zeolites, magnesium carbonate, pumice are mixed with 10 to 75 parts by weight of a water insoluble particulate material, having a weight mean particle size of below 20 microns and an oil absorption 200 to 350 g/100 g, selected from the group consisting of amorphous silicas, low density aluminas and expanded perlites, the resulting blend being agglomerated by compaction.

9. Process according to claim 7 or 8 wherein $TiO_2$ and zinc citrate is added to the amorphous silica particles prior to agglomeration.

10. Process according to claim 7 wherein the agglomeration with water is done with a water:solids ratio of 1.1:1 to 1.35:1.

* * * * *